United States Patent [19]  [11] 3,959,287
Goldstein et al.  [45] May 25, 1976

[54] LIGAND DETERMINATION OF SPIN LABELED COMPOUNDS BY RECEPTOR DISPLACEMENT

[75] Inventors: Avram Goldstein, Stanford; Richard K. Leute, Sunnyvale; Edwin F. Ullman, Atherton, all of Calif.

[73] Assignee: Syva Company, Palo Alto, Calif.

[22] Filed: May 3, 1974

[21] Appl. No.: 466,650

Related U.S. Application Data

[60] Division of Ser. No. 270,108, July 10, 1972, Pat. No. 3,853,914, which is a continuation-in-part of Ser. Nos. 105,535, Jan. 11, 1971, abandoned, and Ser. No. 141,516, May 10, 1971, Pat. No. 3,690,834.

[52] U.S. Cl. .............................. 260/285; 23/230 R; 23/230 B
[51] Int. Cl.² ....................................... C07D 489/04
[58] Field of Search .................... 260/285; 23/230 B

[56] References Cited
UNITED STATES PATENTS

| | | | |
|---|---|---|---|
| 3,453,288 | 7/1969 | McConnell | 260/326.8 |
| 3,489,522 | 1/1970 | McConnell | 23/230 |
| 3,716,335 | 2/1973 | Ullman et al. | 23/230 R |
| 3,799,942 | 3/1974 | Boocock et al. | 260/309.6 |
| 3,850,578 | 11/1974 | McConnell | 23/230 B |

*Primary Examiner*—Alton D. Rollins
*Assistant Examiner*—Diana G. Rivers
*Attorney, Agent, or Firm*—Townsend and Townsend; Bertram I. Rowland

[57] ABSTRACT

Compounds are provided for use in assays of organic compounds, where organic compounds of biological interest are determined at extremely low concentrations by combining in a medium, the composition to be determined, hereinafter referred to as ligand, a high molecular weight material of at least 10,000 molecular weight, which has a site spatially characterisitc of the ligand, hereinafter referred to as receptor, and an analog of the ligand having a free radical functionality hereinafter referred to as "ligand analog". The ligand analog and ligand in the medium compete for the receptor site, the amount of ligand analog bound to the receptor, being dependent on the amount of ligand present in the medium. By following the change in electron spin resonance spectrum of the ligand analog and comparing it to the change in spectrum which would be obtained in the absence of any ligand, the amount of ligand can be determined.

6 Claims, No Drawings

LIGAND DETERMINATION OF SPIN LABELED COMPOUNDS BY RECEPTOR DISPLACEMENT

This is a division of application Ser. No. 270,108, filed July 10, 1972, now U.S. Pat. No. 3,853,914, which application is a continuation-in-part of U.S. application Ser. Nos. 105,535, filed Jan. 11, 1971, now abandoned, and 141,516 filed May 10, 1971, now U.S. Pat. No. 3,690,834.

BACKGROUND OF THE INVENTION

1. Field of the Invention

There is a continuing need for accurate and efficient methods for the rapid analysis of small quantities of organic compounds. Such need is related to widely different areas requiring the determination of minute quantities of organic materials. The need to assay diverse substances, from pollutants in water, soil or air which may be present in extremely small quantities to drugs or naturally occurring physiologically active materials, in body fluids, such as blood, urea and saliva, exemplifies the vast array of situations in which determinations of minute quantities of material are required.

More specifically, both as a medical and police function, the abuse of narcotics and drugs requires an easy method for rapid detection of the use of such drugs, either immediately after ingestion or injection or frequently, after a relatively extended period. The assay should be effective either for the drug, its metabolite, or both, individually or together, and should be specific for the drug being assayed, and not be interfered with by other materials which may be present in the body fluid.

Where the body is malfunctioning, it may be important to assay for particular compounds or metabolites, so as to diagnose the particular malfunction. Also, in case of poisonings, an easy and rapid method for determining the toxin, could be extremely important in providing the antidote.

A wide variety of methods exist for analyzing for a broad spectrum of different organic compounds. Many of these methods are dependent upon different types of detection instruments, such as fluorometers, ultraviolet spectrophotometers. gravimetric analyses, titrimetric analyses, etc. Other methods depend on thin layer chromatography, which is frequently slow, is subject to interference, and may not be reproducible. Because of the significant differences in the procedures, accuracies, and the presence of interfering materials, many diagnostic tests cannot be routinely carried out because of expense and lack of equipment.

2. Description of the Prior Art

The use of free radical probes with naturally occurring materials is found in U.S. Pat. Nos. 3,489,522 and 3,453,288. Labeling of various high molecular weight proteins is described in U.S. Pat. No. 3,481,952. See also Hubbell, et al, Proc. Nat Acad. Sci. U.S., 61, 12 (1968). Organic free radicals have been joined with antibodies and studied. L. Stryer and O. Hayes Griffith, Proc. Nat. Acad. Sci. U.S. 54, 1785 (1965); and J. C. Hsia and L. H. Piette, Arch. Biochem. and Biophys., 132, 466 (1969). In the latter reference, dinitrophenyl antibodies were labeled with 2,4-dinitrophenyl spin labels and the changes in the electron spin resonance (ESR) spectrum were observed as a result of the interaction between the labels and antibodies.

Steroids have been spin labeled by either preparing the oxazole of the 3-keto steroid and oxidizing the nitrogen to the nitroxide or using a carboxyalkyl at the 17 position to form the amide of a tetramethyl(amino)-piperidino-oxyl group. See McConnell, et al., Quart. Rev. of Biophys., 3 91-136 (1970); and Hamilton, et al., Structural Chemistry and Molecular History, W. H. Freeman & Co., San Francisco, Calif. (1968), the chapter on spin labels. See also Hubbell, Proc. Nat. Acad. Sci. U.S. 63, 16 (1963).

See also copending application Ser. No. 794,008, filed Jan. 27, 1969, now abandoned, which discloses the use of nitroxide free radical compounds in determining the changes in pH.

SUMMARY OF THE INVENTION

Spin Labeled compounds (ligand analogs) are provided for use in immunoassays. Biologically active compounds or structural analogs are modified and coupled with a stable free radical compound, so as to provide a ligand analog which: (1) is recognized by a receptor molecule, ordinarily an antibody, and (2) can compete with a biologically active molecule (ligand) for the receptor site in a manner which permits the biologically active molecule to be assayed.

Particularly, biologically active compounds are functionalized or available functional groups employed to link with a stable free radical compound, usually a cyclic nitroxide. The manner of functionalizing and linking to the stable free radical compound provides a product which binds to the receptor specifically and has a binding constant which allows for effective competition with a ligand. Changes in spectrum between ligand analog bound to receptor and unbound ligand analog rotating free in solution permit a quantitative determination of the amount of ligand present, since the ratio of bound to unbound ligand analog is affected by the amount of ligand present in the solution.

DESCRIPTION OF THE SPECIFIC EMBODIMENTS

The compounds of this invention referred to as ligand analogs have three essential parts: (1) a group of atoms forming a moiety recognizable by a receptor and when joined to the other parts, the total has a binding constant to a receptor, which allows for competition between the subject compound and a compound to be assayed (modified ligand moiety); (2) a stable free radical group having an electron spin resonance spectrum which is capable of being detected at low concentrations and which changes in a detectable manner, when bound to a receptor, as contrasted to being unbound and free to rotate in solution (free radical moiety); and (3) a linking group, joining the modified ligand moiety to the free radical moiety, which cooperates with the other parts of the molecule in allowing or enhancing the capability of the moieties joined by the linking group to fulfill their function.

The first part will substantially resemble at least a part of the ligand to be assayed. Usually, the ligand to be assayed will be modified to only a minor degree, for example, by replacement of a proton with a divalent chain, having the other valence bonded to the free radical moiety. However, major changes may be employed, as in the case of a polypeptide where only a portion of the polypeptide may be used for the ligand analog.

The linking group may be simply a single or multiple bond between the modified ligand moiety and the free radical moiety, but will normally be of at least one carbon or heteroatom.

The free radical moiety is conveniently a stable free radical, usually a nitroxide group and usually an $\alpha,\alpha,\alpha',\alpha'$-tetrasubstituted cyclic nitroxide group.

Ligand

Any ligand may be employed which is of biological interest and for which an appropriate receptor may be found having satisfactory specificity for the ligand. The recent literature contains an increasing number of reports of receptors for an increasingly wide variety of biologically active materials. Compounds for which receptors can be provided range from simple phenylalkylamines, e.g., amphetamine, to polymers, e.g., polypeptides and polysaccharides.

The ligands will include such compounds which are narcotics, hypnotics, sedatives, analgesics, antipyretics, anaesthetics, psychotogenic drugs, muscle relaxants, nervous system stimulants, anticholinesterase agents, parasympathomimetic agents, sympathomimetic agents, $\alpha$-andrenergic blocking agents, antiandrenergic agents, ganglionic stimulating and blocking agents, neuromuscular blocking gents, histamines, antihistamines, 5-hydroxytryptamine and antagonists, cardiovascular drugs, antiarrhythmic drugs, antihypertensive agents, vasodilator drugs, diuretics, pesticides (fungicides, antihelminthics, insecticides, ectoparasiticides, etc.) antimalarial drugs, antibiotics antimetabolites, hormones, vitamins, sugars, thyroid and antithyroid drugs, corticosteroids, insulin and oral hypoglemic drugs, and their metabolites.

Included among such drugs and agents are alkaloids, steroids, polypeptides, prostaglandins, catecholamines, xanthines, arylalkylamines, heterocyclics, e.g., thiazines, piperazines, indoles, and thiazoles; amino acids, etc.

Broadly, the ligands will be organic compounds, of from about 100 to 70,000 molecular weight, usually of from about 125 to 40,000 molecular weight, and more usually of from about 125 to 20,000 molecular weight.

A substantial portion of the ligands will be monomers, or low order polymers, usually drugs, hormones and the like, which will have molecular weights in the range of about 100 to 2,000, usually 125 to 1,000. Another significant portion of the ligands will be polymers (compounds with recurring units) which will have molecular weights in the range of from about 750 to 70,000, frequently from 1,000 to 40,000, and usually from 2,000 to 30,000. For polymers of varying molecular weight, weight average molecular weight is intended.

The ligands will normally be composed of carbon, hydrogen, nitrogen, oxygen, sulfur, phosphorous, halogen, and metals, primarily as their cations, such as the alkali and alkaline earth metals and the metals of Groups IB, IIB, VIIB, and VIIIB, particularly the third row of the periodic chart. Most usually, the ligands will be composed primarily of carbon, hydrogen, nitrogen, oxygen, and sulfur.

Structurally, the ligands may be monomers or polymers, acyclic, mono or polycyclic, having carbocyclic or heterocyclic rings. The ligands will have a wide variety of functionalities, such as halo, oxocarbonyl, nonoxocarobnyl, amino, oxy (hydroxy, aryloxy, alyloxy and cycloalyloxy ["alyl" intends a monovalent aliphatic radical], thiooxy, dithio, hydrazo, and combinations thereof.

The most important body of ligands for the purposes of the invention are the haptens. "Substances which on injection do not give rise to antibodies, but which are able to react with antibodies specifically to produce either precipitation or to inhibit precipitation have been termed haptens. This definition has been used to include not only the simple chemical substances which are determinants of specificity when conjugated to protein, and which inhibit precipitation, but also substances obtained from natural sources such as the pneumococcal type specific polysaccharides and dextran which are not antigenic in the rabbit on primary injection." Kabat, et al., Experimental Immunochemistry, Charles C. Thomas, Springfield, Illinois (1967). In the following discussion the term hapten will be confined to non-antigenic groups artificially introduced into proteins which affect specificity and will apply to these groups regardless of whether the group is attached to the protein.

Another group of ligands are those which have naturally occurring receptors. The receptors may be proteins, nucleic acids, such as ribonucleic acid (RNA) or deoxyribonucleic acid (DNA), or membranes associated with cells. Illustrative ligands which have naturally occurring receptors are thyroxine, many steroids, such as the estrogens, cortisone, corticosterone, and estradiol; polypeptides such as insulin and angiotensin II, as well as other naturally occurring biologically active compounds. See Murphy, et al., J. Clin. Endocr., 24, 187 (1964); Murphy, ibid, 27, 973 (1967); ibid, 28, 343 (1968); BBA, 176, 626 (1969); McEwen, et al., Nature, 226, 263 (1970); and Morgan et al, Diabetes, (1966); Page et al., J. Clin. Endocr. 28, 200, (1969).

The ligands may also be categorized by the chemical families which have become accepted in the literature. In some cases, included in the family for the purpose of this invention, will be those physiomimetic substances which are similar in structure to a part of the naturally occurring structure and either mimic or inhibit the physiological properties of the natural substance. Also, groups of synthetic substances will be included, such as the barbiturates and amphetamines. In addition, any of these compounds may be modified for linking to the free radical moiety. These modified compounds are referred to as ligand counterfeits.

A general category of ligands of particular interest are drugs and chemically altered compounds, as well as the metabolites of such compounds. The interest in assaying for drugs varies widely, from determining whether individuals have been taking a specific illicit drug, or have such drug in their possession to determining what drug has been administered or the concentration of the drug in a specific biological fluid.

The drugs are normally of from eight carbon atoms to thirty-five carbon atoms, usually of from nine to twenty-six carbon atoms and from one to ten heteroatoms, usually oxygen, nitrogen or sulfur.

One class of drugs have the following basic functionality:

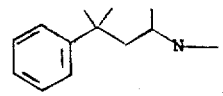

where the lines intend a bond to a carbon atom, and wherein any of the carbon atoms and the nitrogen atom may be bonded to hydrogen, carbon or a heterofunctionality. Drugs which have this basic structure include the opiates such as morphine and heroin, meperidine, and methadone.

Another class of drugs are the epinephrine like drugs which have the following basic functionality:

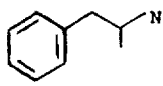

where the lines intend a bond to a carbon atom and wherein any of the carbon atoms and the nitrogen atom may be bonded to hydrogen, carbon or a heterofunctionality. Drugs which have this basic structure include amphetamine, narceine, epinephrine, ephedrine and L-dopa.

The ligand analogs of drugs will usually have molecular weights in the range of 275 to 1,000, more usually in the range of 300 to 700.

Drug ligand analogs

Opiates

The opiates are morphine alkaloids. All of these molecules have the following functionality and minimum structure:

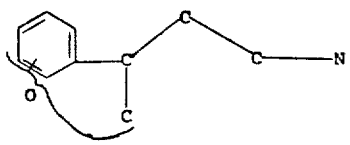

wherein the free valences are satisfied by a wide variety of groups, primarily carbon and hydrogen.

The free radical analog of these compounds will for the most part have the following minimum skeletal structure:

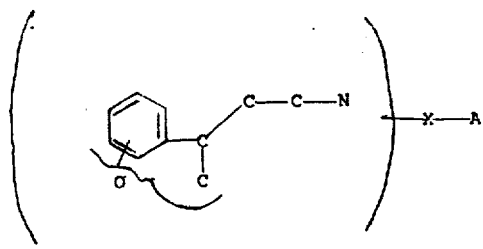

wherein X is a bond or a functionality such as imino, azo, oxy, thio, sulfonyl, oxocarbonyl, nonoxocarbonyl, or combinations thereof. Oxygen will be in the ortho, meta or β position. A will usually be a heterocyclic compound of from 5 to 6 annular members, one of which annular member is a nitrogen of a nitroxide functionality, the other heteroannular member may be oxygen, sulfur or nitrogen. The nitrogen and sulfur may or may not be bonded to an oxygen atom. The ring will have from 0 to 1 site of ethylenic unsaturation. The varous free radical groups will be discussed subsequently.

The molecular weight of the compounds having the free radical substituent will be at least about 350 and normally not exceeding 700, more usually in the range from about 400 to 600.

The free radical labeled morphine and its closely related analogs will have the following formula:

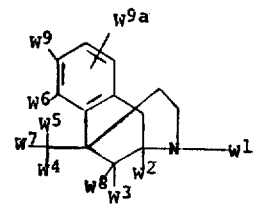

wherein:
any one of the W groups can be $-X^*-A^*$ or an H of any of the W groups may be replaced by $-X^*-A^*$. $X^*-A^*$ will be defined subsequently (there is only one $-X^*-A^*$ per molecule);

$W^1$ is hydrogen or hydrocarbon of from one to eight carbon atoms, particularly alkyl of from one to three carbon atoms, and aralkyl, e.g., methyl and β-phenethyl;

$W^2$ is hydrogen;

$W^3$ is hydrogen;

$W^4$ is hydrogen or taken together with $W^3$ a divalent radical of from 3 to 6 carbon atoms and 0 to 2 oxygen atoms, forming a six membered carbocyclic ring with the carbon chain to which they are attached, e.g., propylene-1,3, 1-hydroxyprop-2-ethylene-1,3, 1-hydroxypropylene-1,3, 1-acetoxypropylene-1,3, 1-acetoxyprop-2-enylene-1,3, 1-oxopropylene-1,3, 1-oxoprop-2-enylene-1,3;

$W^5$ is hydrogen or hydroxyl;

$W^6$ is hydrogen, hydroxyl or taken together with $W^5$ oxy (—O—);

$W^7$ is hydrogen or methyl;

$W^8$ is hydrogen or hydroxyl;

$W^9$ is hydrogen, hydroxy, acyloxy of from 1 to 3 carbon atoms, e.g., acetoxy, (acyloxy intends only carboxy), hydrocarbyloxy of from 1 to 3 carbon atoms, e.g., methoxy, ethoxy, 2-(N-morpholino)ethoxy, and glucuronyl; and $W^{9a}$ is hydrogen.

It is understood, that in all the formulas, except when a minimum or skeletal structure is indicated, unsatisfied valences are satisfied by hydrogen.

(Hydrocarbyl is an organic radical compound solely of hydrogen and carbon and may be saturated or unsaturated, aliphatic, alicyclic, aromatic or combinations thereof).

Preferred compounds have $W^1$, or $W^9$ as $-X^*-A^*$ or have $W^3$ and $W^4$ taken together to provide $A^*-X^*-CHCH_2CH_2-$ or $A^*-X^*-CH=CH-CH-$.

The close morphine analogs will have the following formula:

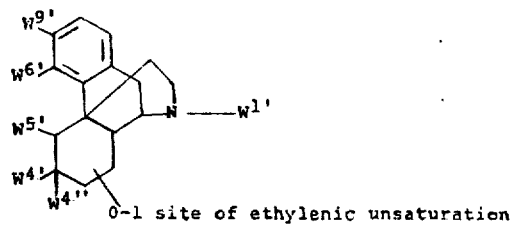

0-1 site of ethylenic unsaturation wherein:
any one of the W groups is $-X^*-A^*$ or an H of any of the W groups can be replaced by $-X^*-A^*$. $X^*-A^*$ will be defined subsequently (there is only one $-X^*-A^*$ per molecule):

$W^{1'}$ is alkyl of from 1 to 3 carbon atoms, e.g., methyl;

$W^{4'}$ is hydrogen, hydroxy, or acetoxy (where two hydroxyls are on the same carbon atom, oxo is intended);

$W^{5'}$ is hydrogen or hydroxyl;

$W^{6'}$ is hydrogen, hydroxyl or taken together with $W^{5'}$ oxy (-O-); and $W^{9'}$ is hydroxy or alkoxy of from 1 to 3 carbon atoms.

Those compounds having the basic morphine structure will have the following formula:

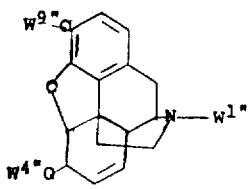

wherein:
one of $W^{1''}$ and $W^{9''}$ is $—X^*—A^*$;
when other than $—X^*—A^*$
$W^{1''}$ is methyl; and
$W^{9''}$ is hydrogen methyl, or glucuronyl;
$W^{4''}$ is hydrogen or acetyl, usually hydrogen;
$X^*$ is

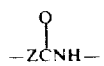

wherein Z is hydrocarbylene of from 1 to 7 carbon atoms, preferably aliphatic, having from 0 to 1 site of ethylenic unsaturation; and $A^*$ is of the formula:

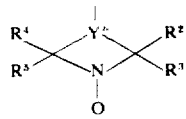

wherein $R^{2-5}$ is alkyl of from 1 to 3 carbon atoms and $Y'$ is a trivalent radical of from 1 to 3 carbon atoms, usually of from 2 to 3 annular carbon atoms, and 0 to 1 heteroatoms.

Illustrative narcotics which can be linked to a free radical compound include morphine, heroin, hydromorphone, oxymorphone, metopon, codeine, hydrocodone, dihydrocodeine, dihydrohydroxycodeinone, pholcodine, dextromethorphan, phenazocine, dionin and their metabolites.

Illustrative compounds which may be bonded to a free radical compound include $O^3$-carboxymethylmorphine, N-(2'-carboxypropyl) $O^3$-methylnormorphine, $O^3$-methyl, $O^7$-morphinyl succinate, 2-aza-2-(2''-phenylethyl)-5,9-dimethyl-6,7-(5'-carboxymethoxybenzo)bicyclo[3,3,1$^{1,5}$]oct-6-ene, $O^3$-ethyl, $O^7$-(3'-aza-5-chloropentyl)morphine, $O^7$-acetyl, $O^3$-carboxymethylmorphine, 7,8-dihydro-14-hydroxymorphinone, O-carboxymethyl oxime, N-desmethyl N-carboxymethylmorphine, N-desmethyl N-3-carboxypropylmorphine, $O^3$-(2'-aminoethyl) morphine and N-desmethyl N-(2-carboxyethyl)morphine.

It is to be understood that the various groups are chosen so as to relate to known compounds of physiological interest. The primary difference between the known compounds and the subject compounds is the linking group and the presence of the free radical moiety.

Of course, many of the compounds which are of interest undergo metabolic changes, when introduced into a vertebrate. The particular physiological fluid which is tested may have little, if any of the original compound. Therefore, the original presence of the compound might only be detectable as a metabolite. In many instances, the metabolite may be the glucuronide, either oxy or oxo derivative of the original compound. In other instances, the original compound may have undergone oxidation, e.g., hydroxylation, reduction, acetylation, deamination, amination, methylation or extensive degradation. Where the metabolite still retains a substantial portion of the spatial and polar geometry of the original compound, it will be frequently possible to make the ligand analog based on either the original compound or metabolite. Where the metabolite is distinctively different than the original compound, the ligand analog will be based on the metabolite.

Since many of the biologically active materials are active in only one stereoisomeric form, it is understood that the active form is intended or the racemate, where the racemate is satisfactory and readily available. The antibodies will be specific for whatever form is used as the hapten.

Free Radical Group (A)

The free radical group is a stable free radical, preferably one which has a fairly simple electron spin resonance spectrum, which can be conveniently bonded through a linking group to the ligand. Various stable free radicals may be used, such as verdazyls, diarylamino radicals, aroxyl radicals, and nitroxide radicals, See Forrester, *Organic Chemistry of Stable Free Radicals*, Academic Press, New York (1968).

In the subject invention, the most versatile compounds are the nitroxide radical compounds, wherein the nitrogen of the nitroxide group is a heteroannular member. These compounds may be mono-or bicyclic, fused or unfused, and will normally be of from 7 to 36 carbon atoms, more usually of from 7 to 16 carbon atoms, wherein the annular members will normally be of from 4 to 9. The compounds may have from 0 to 2 other heteroannular members, more usually from 0 to 1, which are oxygen, nitrogen or sulfur. The nitrogen and sulfur may be bonded to oxygen: nitrogen to one oxygen atom, and sulfur to from 0 to 2 oxygen atoms, more usually 0 or 2. The compounds will normally have from 0 to 1 site of endo ethylenic unsaturation.

A special group of nitroxide compounds are the monoaryl and diaryl nitroxides, where the ortho and para positions are substituted, usually with alkoxy groups, in order to inhibit reaction between the two nitroxide compounds. In the monoaryl nitroxide compound, the other valence of the nitrogen will be bonded to a tertiary carbon atom.

The nitroxide compounds which find use in this invention will have the following formula:

wherein:

α and α′ are organic radicals, which are incapable of forming a double bond to nitrogen without a substantial change in structure and are either aryl, normally trialkoxyaryl, tertiary alkyl, or may be taken together with the nitrogen to which they are attached to form a mono-or bicyclic ring of from 4 to 9 annular members.

For the most part, the compounds which will be employed will have the following formula:

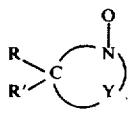

wherein:

R and R′ are hydrocarbon groups of from 1 to 12 carbon atoms, more usually from 1 to 6 carbon atoms, and preferably alkyl of from 1 to 3 carbon atoms; and Y is a divalent functionality of from 3 to 27 atoms other than hydrogen, more usually of from 3 to 12 atoms other than hydrogen, having a total of from 0 to 2 heteroatoms; oxygen, nitrogen or sulfur, which are annular members; Y forms a ring of from 4 to 6 annular members with the carbon and nitrogen atoms to which it is attached. One of the hydrogen atoms bonded to carbon, usually an annular carbon atom, will be replaced so as to provide a site for linking to the ligand.

Y will be bonded to the nitrogen of the nitroxide through carbon, the carbon atom being free of hydrogen or being sterically prevented from forming a double bond to nitrogen, e.g., by an endo double bond.

One preferred group of free radical compounds has the following formula:

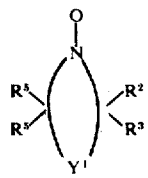

wherein $R^{2-5}$ are the same or different, preferably the same, and are hydrocarbon of from 1 to 12 carbon atoms, more usually of from 1 to 6 carbon atoms, preferably alkyl and particularly preferred methyl; $Y^1$ is a divalent radical having from 1 to 10 carbon atoms, more usually 1 to 4 carbon atoms and from 0 to 1 heteroatoms, there being from 1 to 3 annular members, usually carbon; $Y^1$ may have from 0 to 1 site of ethylenic unsaturation and preferably will form a pyrroline, pyrrolidine, or piperidine ring. The heteroatoms will normally be nitrogen, oxygen and sulfur.

A subgenus of the monocyclic nitroxide is the five membered ring having one annular heteroatom of the following formula:

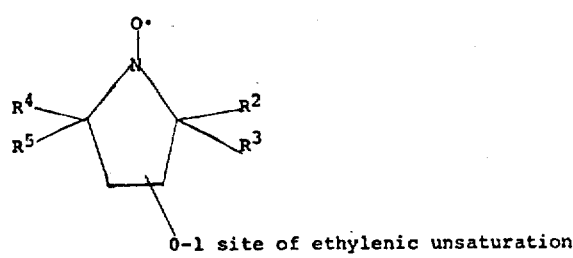

0-1 site of ethylenic unsaturation with $R^{2-5}$ defined as above.

Another subgenus is the six membered ring compounds which have the following formula:

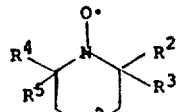

0-1 site of ethylenic unsaturation wherein $R^{2-5}$ are as defined above, and $\alpha^2$ is carbon or nitrogen.

The five membered rings having two annular heteroatoms will for the most part have the following formula:

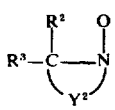

wherein $Y^2$ is

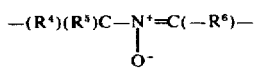

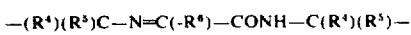

wherein $R^{2-5}$ are as defined above, $R^6$ and $R^7$ may be the same as $R^{2-5}$ or hydrogen.

A preferred nitroxide free radical containing group of compounds has the following formula:

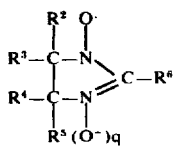

wherein $q$ is 0 or 1, preferably 1. when q is 1, the nitrogen to which the oxygen is bonded is positive, $R^{2-5}$ have been defined previously, and $R^6$ is as defined above.

Illustrative rings include 1-oxylpiperidine, 1-oxylpyrrolidine, 1-oxylpyrroline, 1-oxylimidazolidine, 1-oxyl-3-oxyimidazolidine, 1-oxyltetrahydropyridine and 3-oxyloxazolidine.

The bridgehead nitroxide compounds will for the most part have the following formula:

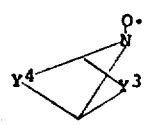

wherein:

$Y^3$ and $Y^4$ are divalent aliphatic hydrocarbon radicals having from 0 to 1 site of ethylenic unsaturation and of from 2 to 3 carbon atoms.

The last nitroxide to be specifically considered is the aryl nitroxide which will have the following formula:

wherein:

α³ is 2,4,6-trialkoxy benzene, wherein the alkoxy groups are of from 1 to 3 carbon atoms and α⁴ is the same as α³ or tertiary alkyl of from 4 to 12 carbon atoms, more usually of from 4 to 6 carbon atoms.

The verdazyls will for the most part have the following formula:

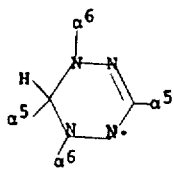

wherein:

α⁵ is hydrocarbon or a acyloxy of from 1 to 8 carbon atoms and α⁶ is aryl or substituted aryl, e.g., hydroxy or amino of from 6 to 10 carbon atoms.

As already indicated, the free radical group is bonded to the ligand through a bond or linking group which is substituted on the free radical group by replacing one of the hydrogen atoms. In addition, sharper spectra can be obtained by replacing hydrogen atoms with deuterium atoms. It is therefore, to be understood when hydrogen is spoken of in referring to the free radical group that deuterium is to be treated as an equivalent.

In carrying out the subject invention, particularly where the ligand does not have a naturally occurring receptor or it is found to be more convenient to prepare antibodies, the ligand will be modified by providing a group which can be bonded to a protein. Therefore, some reactive functionality will be introduced into the ligand, either by activating a functionality which is present, e.g., by transforming a carboxylic acid to a mixed anhydride, or by introducing a new functionality, e.g., modifying a hydroxy group with a carboxymethyl group. Since the antibodies which are formed will recognize the ligand with its attached linking group, that was employed in preparing the antigenic material, normally the same ligand with its attached linking group used to prepare the antigenic material will also be used to bond to the free radical group. Therefore, most commonly, the substituents on the free radical group will be the relatively simple substituents such as amino, hydroxy and carboxy.

Illustrative compounds which will be used for linking to the ligand are 1-oxyl-3-amino-2,2,5,5-tetramethylpyrrolidine, 1-oxyl-3-hydroxy-2,2,5,5-tetramethylpyrrolidine, 1-oxyl-3-carboxy-2,2,5,5-tetramethylpyrrolidine, 1-oxyl-3-carboxy-2,2,5,5-tetramethylpyrroline, 1-oxyl-4-amino-2,2,6,6-tetramethylpiperidine, 1-oxyl-4-hydroxy-2,2,6,6-tetramethylpiperidine, 1-oxyl-4-carboxy-2,2,6,6-tetramethyltetrahydropyridine, 2-methylamino-1,3-dioxy-4,4,5,5-tetramethylimidazoline, 2-hydroxymethyl-1,3-dioxy-4,4,5,5-tetramethylimidazoline and 1-amino-7-oxyl-7-azabicycloheptane.

In many instances, it may be advantageous to have a reactive group on the free radical group and bond that to the ligand. Whenever possible, this group would provide the same type or possibly even the same functional bridge to the ligand. In effect, it could merely be the reverse situation, the final compound being the same as if the linking group had been present in reverse on the ligand. For example, if there is an amino group on the ligand, it would be possible to modify the ligand group so as to form an isocyanate. Similarly, if there is an amino group on the free radical, it is also possible to modify that amino group to form an isocyanate. The bridge will be the ureylene, irrespective of which procedure was used.

Illustrative compounds which can be used for linking the free radical functionality to the ligand are 1-oxyl-2,2,5,5-tetramethyl-3-isocyanatopyrroline, 1-oxyl-2,2,5,5-tetraethyl-3-isothiocyanatopyrrolidine, N-(1-oxyl-2,6-dimethyl-2,6-dibenzylpiperidin-4-yl) succinamic acid, N-(1-oxyl-2,2,5,5-tetraethylpiperidin-4-yl) maleamic acid, N-(1-oxyl-2,2,5,5-tetrabutylpyrrolidin-3-yl) oxalamic acid, mono-(1-oxyl-2,2,5,5-tetramethylpiperid-4-yl) fumarate, N-(1-oxyl-2,2,5,5-tetramethylpiperid-4-yl) glycine, 1-oxyl-2,2,5,5-tetramethylpyrrolid-3-ylsulfonylacetic acid, 1-oxyl-2,2,5,5-tetramethyl-3-hydroxypyrrolidine, 1-oxyl-2,2,5,5-tetramethylpyrrolin-3-ylcarboxylic acid, N-(1-oxyl-2,2,5,5-tetramethylpyrrolidin-3-yl) terephthalamic acid, 1-oxyl-2,2,5,5-pyrrolidin-3-yl malonate, 1-oxylpyrrolin-3-yl-3,5-dispiro-(1'-cyclopentane) carboxylic acid, 4,4,5,5-tetramethyl-1,2,3,-trioxyimidazoline, 4,4,5,5-tetrapropyl-2-bromomethyl-1-oxyl-3-oxide-imidazoline, 4,4,5,5-tetrabenzyl-2-(p-aminophenyl)-1-oxyl-3-oxide-imidazoline, 4,4,5,5-tetramethyl-2-chlorosulfonylmethyl-1-oxyl-3-oxide-imidazoline, 4,4,5,5-tetramethyl-2-carboxymethyl-1-oxyl-3-oxide-imidazoline, 5,6-dimethyl-4,5-(butylene-1, 4)-2-isocyanatomethyl-1-oxyl-imidazoline, 4,4,5,5-tetramethyl-2-carboxycarbonyl-1-oxyl-3-oxide-imidazoline, and 2-chlorocarbonyl-1-oxyl-3-oxide-imidazoline-4,5-dispiro(1'-cyclohexane).

Linking Groups

The group —X*— will vary depending on the available sites for preferably 1, when on A*. For the most part, the available groups on the ligand, either naturally present or introduced, will be hydroxyl (—OH); amino

where R⁸ will usually be hydrogen or alkyl of from 1 to 6 carbon atoms); mercapto (—SH); oxo (—C=O); carboxy (—CO₂H); and methine ( CH), where the H is bonded, usually to an aromatic carbon atom and preferably the ring is activated by oxy or amino substituents.

The primary function of the linking group is to bond the free radical to the liquid within a relatively short distance of each other. However, the linking group may also be used to fulfill other functions, such as to modify the solubility properties of the final product. Particularly, when relatively large hydrophobic groups are employed, as in steroids, a group capable of forming a salt may be introduced into the linking group. Illustrative groups are carboxylates, sulfonates, sulfates and quaternary ammonium salts. The counter ion may be any convenient ocunter ion, preferably monovalent, such as chloride, fluoride, alkali metal salt, ammonium etc.

The linking group will usually be of from 0 to 8 carbon atoms, more usually of from 0 to 6 carbon atoms and from 1 to 8 heteroatoms, more usually of from 1 to 6 heteroatoms which are oxygen, sulfur and nitrogen, more usually oxygen and nitrogen. Any counter ion to a salt forming group is not to be counted in the number of hetero atoms. The preferred groups are the nonoxocarbonyl or thiocarbonyl, alkylamino or alkoxy as linking functionalities.

The chain length of the linking groups is preferably from 1 to 10 atoms, usually 2 to 6 atoms or the equivalent, when cyclic structures are involved.

A linking group that finds particular use is the hydrocarbylcarboxamido or oxyhydrocarbylcarboxamido of from 2 to 8 carbon atoms, usually of from 2 to 6 carbon atoms and from 0 to 1 site of aliphatic unsaturation. Usually the hydrocarbylene is aliphatic and will be represented by Z in the following formulas.

The following tabulation indicates the various linking groups, varying with the functionalities present on the ligand and the free radical.

wherein:

$R^9$ is hydrogen or hydrocarbon of from 1 to 6 carbon atoms;

T is oxygen, sulfur, or NR', wherein R' is hydrogen or hydrocarbon of from 1 to 6 carbon atoms, usually H, T is usually oxygen;

Z' is alkylidenyl

Z is a bond; hydrocarbon of from 1 to 10 carbon atoms, more usually alkylene of from 1 to 6 carbon atoms, alkenylene of from 2 to 6 carbon atoms, alkynylene of from 2 to 6 carbon atoms, cycloalkylene of from 4 to 10 carbon atoms, arylene of from 6 to 10 carbon atoms, oxaalkylene of from 4 to 8 carbon atoms, and azaalkylene of from 4 to 8 carbon atoms.

When the linking functionality is hydroxyl, Z or a nonoxocarbonyl bond to the hydroxy is preferred, particularly Z.

When the linking functionality is amino, nonoxocarbonyl, the sulfur and nitrogen analogs, or Z are preferred, particularly nonoxocarbonyl.

| Ligand | Free Radical |
|---|---|
| (hydroxyl (—O—); amino(—N(R⁹)) | (hydroxyl (—O—); amino(—N(R⁹)) |
| $-\overset{T}{\underset{\|}{C}}-$ | |
| $-\overset{T}{\underset{\|}{C}}-Z-\overset{T}{\underset{\|}{C}}$ | |
| $-Z-\overset{T}{\underset{\|}{C}}-$ | |
| $-\overset{T}{\underset{\|}{C}}-Z-$ | |
| —SO₂—Z—SO₂ | |
| $-\overset{T}{\underset{\|}{C}}-Z-SO_2$ | |
| $-SO_2-Z-\overset{T}{\underset{\|}{C}}$ | |
| —Z—SO₂ | |
| —SO₂—Z | |
| =Z'— | |
| —Z— | |

| Ligand | Free Radical |
|---|---|
| (oxocarbonyl(—C=O)) | (hydroxy(—O—); amino (—N(R⁹)—) |
| =N—O—Z | |
| =N—O—Z—CT | |
| =N—O₂CZCT— | |
| =CHCH— | |
| =NNH—Z—CT— | |

| Ligand | Free Radical |
|---|---|
| (nonoxocarbonyl(—C(=O)—) | (hydroxy(—O—); amino (—N(R⁹)—) |
| —O—Z—CT | |
| —N(R⁹)—Z—CT— | |
| —N(R⁹)—Z— | |

-continued

| Ligand | Free Radical |
|---|---|
| | —O—Z— |

| Ligand | Free Radical |
|---|---|
| (methine( CH )) | (hydroxy(—O—); amino (—N(R⁹)—) |
| | —N₂—Z″— |
| | —N₂—Z″—CT— | wherein Z, T, and $R^9$ are as defined previously and $Z''$ is arylene of from 6 to 10 carbon atoms.

Where the free radical group has a carboxy functionality (nonoxocarbonyl), the groups would then be

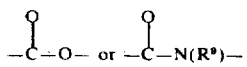

where the oxygen and nitrogen are bonded to any of the linking groups indicated above, and where Z or $Z''$ is bonded to the oxygen or nitrogen.

Where the free radical has an oxocarbonyl group and the ligand and hydroxy or amino group, one need only reverse the linking group for the oxocarbonyl on the ligand and hydroxy or amino on the free radical group.

The following table indicates the linking groups for oxocarbonyl being present in the free radical and other than hydroxy or amino on the ligand, the symbols having been defined previously.

| Ligand | Free Radical |
|---|---|
| (oxocarbonyl(—C=O)) | (oxocarbonyl(—C=O)) |
| | =N—O—Z—N= |
| | =N—O₂C—Z—CO₂N= |
| | =N—O—Z—CO₂N= |
| | —NNH—Z—NHN= |

| Ligand | Free Radical |
|---|---|
| (nonoxocarbonyl(—C=O)) | (oxocarbonyl(—C=O)) |
| | —O—Z—O—N= |
| | —N(R⁹)—Z—O—N= |
| | —O—N= |
| | —O—Z—HNN= |
| | —N(R⁹)—ZHNN= |

| Ligand | Free Radical |
|---|---|
| (methine(=CH—)) | (oxocarbonyl(—C=O)) |
| | —N₂—Z″—O—N= |
| | —N₂—Z″—NHN= |
| | —N₂—ZCO₂N= |
| | —N₂—ZCTNHN= |

The preferred Z groups (Z, Z' and Z'') are hydrocarbylene having from 0 to 1 site of aliphatic unsaturation, e.g., ethylenic. Hydrocarbylene is a divalent radical composed solely of carbon and hydrogen, which may be aliphatic, alicyclic, aromatic or combinations thereof, e.g., aralkyl.

Where the ligand has a mercapto group, the maleimide functionality is particularly useful, where the imide nitrogen is either directly bonded to the free radical group, or bonded through the functionalities described above, e.g., carboxymethyl.

While for the most part, the free radical functionality may be bonded to any convenient position of the ligand, either through a functionality naturally present in the ligand or one introduced synthetically, there are preferred methods of bonding the free radical functionality to the ligand. First, it should be recognized that the free radical substituted ligand need not have any biologic activity. One is solely concerned in not disturbing the geometry and polar site relationships of a substantial portion of the molecule. Therefore, assuming synthetic convenience, the free radical functionality will normally be introduced at one end of the molecule.

Furthermore, if one is attempting to assay one of a variety of molecules which are quite similar, for example steroids, but differing in their substituents at the 17 position, one would choose to mark the molecule with the free radical functionality at a site distant from the functionality, which provides the distinction between the compound to be assayed and similar compounds which may also be present in the composition which is being assayed. For example, in assaying for steroids, it would frequently be preferable to bond at the 3 or 6 position rather than at the 17 position, since the distinctive portion of the molecule is normally at the 17 position, the 3 position for the most part remaining the same or differing in being an alcohol or a ketone with most steroids.

Also, it may be found that better binding with a receptor is achieved by having the free radical functionality bonded to one site rather than another site. This can be readily determined by preparing a number of free radical modified ligand compounds and determining their equilibrium concentration with the receptor. This is particularly true where the ligand is a hapten. Almost invariably, the site of the ligand, and usually the linking group, will be the same for bonding the ligand to the protein as the ligand to the free radical. In this way, that portion of the ligand molecule which extends from the protein and is the most likely portion of the molecule to provide a template for the antibodies, is the same portion of the molecule which remains unmodified by the linking group to the free radical group.

For an excellent discussion of linking groups for steroids, for conjugation to proteins, see Peron, et al., Immunologic Methods in Steroid Determination, Appleton, Century Crofts, New York 1970.

RECEPTOR

In the subject invention, for the most part, the receptors will be macromolecules which have sites which recognize specific structures. The recognition of the specific structures will be based on van der Waals forces, which provide a specific spatial environment which maximizes the van der Waals forces; dipole interactions, either by permanent or induced dipoles; hydrogen and ionic bonding; coordinate covalent bonding; and, in some cases, covalent bonding. For a detailed discussion of mechanisms by which receptors bond ligands, see Goldstein, et al., Principles of Drug Action, Harper and Rowe, New York 1968.

The macromolecules of greatest interest are proteins and nucleic acids which are found within cells, blood, and other biological fluids. These compounds include enzymes, antibodies, ribonucleic acid (RNA) and deoxyribonucleic acid (DNA), carrier proteins, such as transcortin, thyroid binding globulin (TBG), thyroid binding prealbumin (TBP), and "bound" receptors (that is, receptors bound to cell membranes).

The most convenient group of proteins for use in the subject invention are antibodies. These materials are conveniently used in the analysis of the category of ligands referred to as haptens. Antibodies are produced by introducing an immunogenic substance into the bloodstream of a living animal. The response to the introduction of the immunogenic substance or antigen is the production of antibodies which act to coat the antigen and detoxify it or precipitate it from solution. The antibodies form a coat which is geometrically arranged so as to fit the spatial arrangement of the antigen. This may be analogised to a lock and key. The interaction is normally reversible, in that the antigen is subject to displacement or removal by various means without destruction of the receptor site.

There are many materials which are antigens and will produce an immunogenic response by being introduced into the bloodstream of a mammal. However, a number of materials of interest are not antigens, but are haptens, and in that situation, an extra step in preparing the antibody is required. This method of preparing antibodies with materials other than antigens is well known and may be found in Microbiology, Hoeber Medical Division, Harper and Rowe, 1969. See also, Landsteiner, Specificity of Serological Reactions, Dover Publications, N.Y. 1962; Kabat, et al., Experimental Immunochemistry, Charles C. Thomas, Springfield, Ill., 1967; and Williams, et al, Methods in Immunology and Immunochemistry, Vol. I, Academic Press, New York, 1967.

The material which is to be assayed is bonded to a protein by any convenient means and the modified protein introduced into the bloodstream. The same type of bonding groups used with the free radical attachment to the ligand may be employed. The antibodies which form will include groups of antibodies which are shaped to fit the foreign moiety (hapten) bonded to the protein. Therefore, antibodies are obtained which are specific to the compound or hapten bonded to the protein. By careful separation techniques, the antibodies primarily concerned with the hapten in question, can be concentrated so as to provide an antibody composition which is primarily related to the specific hapten which was bonded to the protein.

To illustrate this method, para-aminobenzene arsonate is diazotized to form the diazo salt. By combining the diazo salt with rabbit globulin, the rabbit globulin is labeled with para-azobenzene arsonate. By introducing this composition into the bloodstream of an animal other than a rabbit, for example, a sheep, antibodies can be formed which will have a spatial arrangement which recognizes the azobenzene arsonate.

In addition to antibodies, there are a number of naturally occurring receptors which are specific to compounds of biological interest. Compounds for which receptors are naturally occurring include thyroxine, corticosterone, cortisone, 11-desoxycortisol, 11-hydroxyprogesterone, estrogen, insulin and angiotensin. See, for example, Vonderhaar, et al., Biochem. Biophysics Acta, 176, 626 (1969). All of these ligands have been studied and reported upon in the literature in connection with studies on their binding with specific receptors.

If desired, the antibodies may be bonded to a variety of supports. The bonding may be carried out similarly to that employed for bonding the protein to a ligand. Various supports include polyacrylamides, copolymers of vinyl acetate and acrylic acid, polyvinyl esters, modified cellulose, Agarose, Sepharose, etc. The value of the support, is that the antibody may be easily separated from the solution in this manner and the clear solution analyzed. Therefore, the spectrum resulting from any of the radical absorbed on the antibody will not be present in the assay. An illustrative support is para-aminobenzamidoethyl-Bio-Gel P-60 supplied by Bio-Rad Laboratories of Richmond, Calif.

Method

The method employing the compounds of this invention is concerned with determining the amount of a specific material "ligand" - in a solution by bringing together a high molecular weight material having a site characteristic of the polar nature and spatial geometry of the ligand to be determined - "receptor" - and a free radical analog of the ligand - "ligand analog" -. The electron spin resonance spectrum of the free radical functionality will vary when associated with a relatively small molecule, as compared to being associated with a substantially larger molecule. In a solution containing only ligand analog and receptor, at equilibrium the receptor sites will be substantially filled with ligand analog. Upon adding a small amount of ligand to the solution, the ligand and ligand analog will compete for the deficiency of receptor sites, affecting the position of the equilibrium and the appearance of the spectrum. By using known amounts of ligand, the effect on the equilibrium can be readily determined, as seen by the change in the electron spin resonance spectrum. Once the standards have been calibrated, various devices can be employed which will provide a reading indicating directly the amount of the unknown material.

In carrying out the assay, three basic reagents are involved: the unknown or ligand; the free radical analog; and the receptor. The free radical analog and the receptor are conveniently prepared as reagent solutions, with additional reagents, as required, being in one or both of the solutions. Reagents may be transported either dry or in solution. Liquids are convenient for the transfer of small amounts of materials, since they are readily metered.

Polar solvents will normally be used, particularly hydroxylic solvents, such as water and aqueous alkanols of from 1 to 2 carbon atoms (methanol and ethanol). Other oxygenated solvents may also be employed, such as ethers, esters, dimethyl formamide, dimethyl sulfoxide, hexamethyl phosphoramide, etc., usually in combination with water in amounts of 0 to 40, more usually 1 to 30 volume percent.

In carrying out the assay, the dilution factor for each reagent will usually be 1.5 t0 10, more usually 1.5 to 5. Therefore, the original concentration of the reagent in the reagent solution will to some extent anticipate the final concentration of the reagent in the assay.

The concentration of the receptor in the reagent solution will usually be in the range of $10^{-9}$ to $10^{-3}$ M, preferably $10^{-7}$ to $10^{-3}$ M, based on active sites: (The method of determination of active sites will be described in the experimental section.) Usually, this will roughly be about $10^{-4}$ to 100 mg/ml, more usually, about $10^{-2}$ to 10 mg/ml. For the assay, the concentration of receptor sites, should be about $10^{-3}$ t0 $10^{-9}$ M, more usually $10^{-4}$ to $10^{-8}$ M.

The molar concentration ranges for the ligand analog will parallel those of the receptor, both as to the reagent solution and as to the assay concentration. The ratio of ligand analog to receptor will usually be from 0.5 to 10, more usually 0.5 to 3 molecules per receptor site. The ratio will be governed by the binding constants, the method of determination, the suspected concentration of ligand and the specificity of the assay.

Usually, it will be desirable to have the assay mixture buffered, so as to have a mixture with a pH in the range of 5.0 to 10.5, preferably 7.0 to 8.5. The concentration of buffer will vary with the buffer, usually in the reagent solution being about 0.05 to 0.8 M, more usually 0.2 to 0.7 M. The more acid the unknown solution, the higher the pH of the reagent solution which is used. In the assay mixture, the buffer concentration will usually be about 0.1 to 0.6 M.

The choice of buffer will vary widely, depending on its effect on the reagents, e.g., solubility, inertness to the reagents, etc. Various buffers which are commonly used include tri(hydroxymethyl)methyl amine (Tris); alkali metal and ammonium borates, e.g., sodium borate; alkali metal and ammonium phosphate e.g., sodium and disodium phosphate; alkali metal bicarbonate and carbonate, e.g., sodium bicarbonate and carbonate; ethylenediaminetetraacetic and, amine diols in combination with their salts, e.g., 2-amino-2-methyl-1,3-propandiol hydrochloride; ammonium chloride-ammonium hydroxide combination; barbital-alkali metal barbital combination; heterocyclic amines in combination with their salts, e.g., collidine-hydrochloric acid, collidine-pyridine-acetic acid, ethanolamine-hydrochloric acid, N-ethylmorphine-pyridine-acetic acid, glycine-hydrochloric acid, piperazine-glycylglycine, etc. The preferred buffers are Tris, bicarbonate-carbonate, phosphate and borate. With the inorganic buffers, it is frequently convenient to neutralize the inorganic acid, e.g., boric acid, with an alkali metal base, eg., sodium hydroxide, to the desired pH.

Other salts or reagents may also be present in the reagent solution, as required.

In some instances, pretreatment of the unknown substrate may be required. Where the unknown is suspected of containing a reductant, e.g., ascorbic acid, which is capable of reducing the free radical, the unknown substrate may be treated with an oxidizing agent, such as sodium dichromate, sodium perborate, sodium periodate, iodine, etc. The choice of oxidizing agent will be governed by its effect on the other reagents which will be present in the assay. Alkali metal dichromate, particularly sodium dichromate and sodium hypoiodite, are oxidants of choice. The amount of oxidant will be governed by the suspected amount of reductant. With urine, concentrations of $10^{-1}$ to $10^{-3}$ M will usually suffice.

The order in which the reagents are brought together will be relatively arbitrary, governed to some degree on the interaction between the free radical ligand analog and the receptor. Therefore, the free radical ligand analog may be used bound to the receptor, and the unknown solution added. Or, the unknown solution and free radical ligand analog may be added simultaneously to compete for the sites on the receptor. In some instances, the ligand may first be bound to the receptor, and the ligand analog added. Any of these methods can be accurately calibrated and used for determination of a particular ligand. When convenient, the solution may be separated from the receptor, and the concentration of the free radical ligand analog in the solution determined. This can also be related to the unknown ligand concentration.

The solutions are mixed to provide reasonable homogeneity and, if necessary, transferred to an electron spin resonance sample holder. The holder is then introduced into an electron spin resonance spectrometer cavity. The temperature in the cavity is normally maintained in the range of about 15° C to 40° C, and the change in the spectrum metered. Depending on the method of standardization and method of calibration, one or more points may have to be determined in order to determine the concentration of the unknown ligand.

Extremely small volumes are employed for the determination, usually in the range of 10 to 100 $\mu$l for the total volume of reagents and unknown. The amount of unknown ligand that is required will normally be in the range of about $10^{-5}$ to $10^{-15}$ moles, more usually $10^{-7}$ to $10^{-13}$ moles.

A modification, which adds an additional procedural step, is to have the receptor bound to a support. This normally involves a heterogeneous system, rather than a homogeneous system. In many instances the advantageous use of the support in a heterogeneous system, more than offsets the additional effort involved in bonding the receptor to the support.

One way in which the support could be used is to pack a column (a column would probably be a small capillary tube) with the receptor bound to the support, and then bind ligand analog to the receptor. The amount of ligand analog present could be determined by measuring the electron spin resonance spectrum of the column, or preferably measuring the amount of ligand analog in solution before and after passage through the column. Now, relatively large amounts of the unknown fluid could be passed through the column, followed by determining the spectrum of the column or of the effluent. The change in spectrum would be proportional to the amount of ligand in the fluid passed through the column. (Also the rate of flow if equilibrium is not established.)

Alternatively, one could mix ligand and ligand analog, with the receptor bound to the support in a tube. After equilibrium was established, by separating the receptor bound to the support from the supernatant liquid, one could measure the electron spin resonance of either or both, the support or the supernatant liquid. A further variation, would be to determine the remaining ligand analog bound to the support by addition of ligand to the support, so as to release any remaining ligand analog and to analyze for the ligand analog in solution.

In addition, supports will find particular use, when a large molecule usually in excess of 5,000 molecular weight, and more usually in excess of 10,000 molecular weight, is the ligand to be assayed. It is found, that when the free radical compound is bonded to a large molecule, significantly in excess of 5,000 molecular weight, the spin approximates that of an immobilized spin in solution. Therefore, further binding to a receptor, does not significantly change the spin of the free radical. It is thus appropriate to bind the receptor to the support, carry out the assay by adding ligand analog and ligand to the support and then determining the amount of ligand analog in a solution and/or on the support. In this instance, one is not determining the change in electron spin resonance spectrum due to change of immobilized spin to mobilized spin, but rather the absolute number of free radical groups which are present.

In order to demonstrate the broad spectrum of compounds which may be assayed, a number of different haptens of distinctively different structure and polar nature were used and bonded in a variety of ways to different nitroxide containing radical compounds. These compounds are not antigens and were therefore bonded to proteins which are then used for the formation of antibodies. The antibodies are shown as being used both with and without supports.

Experimental

The following examples are offered by way of illustration and not by way of limitation.

(All the temperatures are reported in Centigrade)

| A. | Preparation of rabbit serum and γ-globulin | |
| --- | --- | --- |
| B. | Isolation of antibodies | 90 |
| C. | Binding of antibodies to support | 91 |
| 1.1 | 3-[2'-(2'',4''-Dinitroanilino) acetamido]-2,2,5,5-tetramethylpyrrolidinyl-1-oxyl | 92 |
| 1.2 | 3-[3'-(2'',4''-Dinitrophenylamino)propyl]carbamoyl 2,2,5,5-tetramethylpyrrolidinyl-1-oxyl | 93 |
| 1.3 | 4'(2',4'-Dinitroanilino)-2,2,6,6-tetramethylpiperidino-1-oxyl | 94 |
| 2.1 | 3-[2'-(O$^{3'}$-Morphino)acetamido]-2,2,5,5-tetramethylpyrrolidinyl-1-oxyl | 95 |
| 2.2 | 4-[2'-(O$^{3'}$-Morphino)acetamido]-2,2,6,6-tetramethylpiperidino-1-oxyl | 96 |
| 2.3 | 3-(O$^{3'}$-Morphinomethyl)-2,2,5,5-tetramethylpyrrolinyl-1-oxyl | 97 |
| 2.4 | 3-(O$^{3'}$-Morphinoacetamido)-2,2,5,5-tetramethylpyrrolidinyl-1-oxyl | 98 |
| 2.5 | 3-[2'-(O$^{3'}$-Morphino)butyramido]-2,2,5,5-tetramethylpyrrolidinyl-1-oxyl | 100 |
| 2.6 | 3-(2'-(O$^{3'}$-Morphino)-3'-methylbutyramido)-2,2,5,5-tetramethylpyrrolidinyl-1-oxyl | 103 |
| 2.7 | O$^3$-(Carbomethoxyhexamethylene-)morphine | 106 |
| 2.8 | 3-[(N-Normorphino)acetamido]-2,2,5,5-tetramethylpyrrolidinyl-1-oxyl | 108 |
| 2.9 | Conjugation of carboxymethyl morphine with poly-L-lysine (PLL) | 112 |
| 2.10 | Conjugation of carboxymethyl morphine to bovine serum albumin (BSA) | 114 |
| 2.11 | Conjugation of N-carboxymethylnormorphine to bovine serum albumin (BSA) | 115 |

EXAMPLE A

Preparation of Rabbit Serum and γ-Globulin

Antisera may be obtained as follows: The antigen (hapten coupled to an appropriate protein) is made up in a saline solution (9 g/liter) at a 2 mg/ml concentration. Per 1.0 ml aliquot of the above solution introduced, there is introduced simultaneously 3 ml of Complete Freund's Adjuvant in homogenized form by means of a two-way needle. For subcutaneous injections, approximately 0.3 ml (antigen + Freund's solution) is injected per site and for intraperitonealy injections, approximately 0.4 ml is injected. The total dosage is about 4.0 ml per rabbit.

After 3 to 4 weeks, a booster shot is given intramuscularly consisting of 0.5 ml of the above saline solution and 0.5 ml of Complete Freund's Adjuvant. A period of 5 to 7 days is allowed to pass and the rabbit is bled by heart puncture.

When the desired amount of blood is collected, the blood is allowed to clot and the clot removed. The remaining solution is then centrifuged at 2,000 rpm for 10 minutes. The serum is collected free of loose red cells.

An equal volume of saturated ammonium sulfate solution is added to the serum dropwise with stirring at 4°. After standing for 1 hour at that temperature, the solution is centrifuged at 10,000 rpm for 15 minutes and the supernatant removed. The residue is suspended in as small a volume as possible of 1X PBS (phosphate buffered saline, see below for description), transferred to a dialysis bag and dialyzed overnight against 1X PBS pH 7.0. The residue in the dialysis bag is then isolated and frozen.

(To make 1 l. of 10X PBS combine 76.5 g NaCl, 7.25 g Na$_2$HPO$_4$ (anh.), 2.12 g of KH$_2$PO$_4$ and 10.0 g of

EXAMPLE B

Isolation of Antibodies

In 20 ml of dimethyl formamide was introduced 400 mg aminoethyl-Bio-Gel-P-60 and 300 mg of carboxymethyl morphine (See Example 2.4) and 1 g sodium bicarbonate added. After stirring the suspension for two days at 4°, the suspension was filtered, the residue washed with water until the washings were neutral, and then the residue was dried in vacuum.

The resulting product was then suspended in 20 ml rabbit serum containing morphine antibodies and stirred for 4 hours at 4°. Filtration gave a residue which was resuspended in 5 ml phthalate buffer, pH 3.8 (0.1M) and stirred for 2 hours. The gel was separated by centrifugation and the supernatant liquid dialyzed against phosphate buffer, pH 7.4 (0.1M) to give a buffered solution of substantially pure antibodies.

EXAMPLE C

Binding of antibodies to support

A. Para-aminobenzamidoethyl-Bio-Gel P-60 (50 mg) was suspended in 10 ml of water and acidified with 1N hydrochloric acid to pH 4.5. The suspension was cooled to 4° and 6 mg sodium nitrite dissolved in 2 ml water added over a period of 10 minutes. A one ml portion of $10^{-5}$ M solution of purified morphine antibodies was mixed with the above material at pH 9 while maintaining the temperature. After 40 minutes, 20 mg resorcinol was added to scavenge the remaining diazonium compound. The solid was then filtered and washed with pH 8 borate buffer.

B. The above supported morphine antibodies (50 mg) were suspended in 10 ml of pH 8 borate buffer solution $10^{-4}$ M in 4-[2'-($O^{3''}$-morphino)acetamido]-2,2,6,6-tetramethylpiperidino-1-oxyl and stirred for 2 hours. Filtration and washing with water gave a solid (50 mg) which showed broad ESR signals indicating the binding of the free radical labeled morphine to the receptor.

EXAMPLE 1.1

3-[2'-(2'',4''-Dinitroanilino)acetamido]-2,2,5,5-tetramethylpyrrolidinyl-1-oxyl 3-Glycylamido-2,2,5,5-tetramethylpyrrolidinyl-1-oxyl (250 mg) was dissolved with stirring in 2 ml methanol. Potassium bicarbonate (0.5 g) was added followed by 0.5 ml of 2,4-dinitrofluorobenzene. Gas evolution subsided after 1 hour whereupon the solution was diluted with 10 ml of water and extracted with three 15 ml portions of chloroform. The combined organic layers were dried over anhydrous magnesium sulfate, filtered and evaporated. The oily residue was chromatographed on silica gel with 500 ml of chloroform followed by 250 ml of 1:1 chloroform/acetone. Evaporation of the solution and recrystallization of the residue by addition of benzene yielded 370 mg (86 %). m.p. 125°–127° (decomp.) (recrystallization from 5 ml of ethyl acetate). Anal. Calcd. for $C_{16}H_{22}N_5O_6$: C, 50.52; H, 5.82; N, 18.41. Found: C, 50.45; H, 5.89; N, 18.17. M.W. 380.396 ESR spectrum $a_N$ = 14.1 Gauss (benzene)

EXAMPLE 1.2

3-[3'-(2'',4''-Dinitrophenylamino)propyl]carbamoyl-2,2,5,5-tetramethylpyrrolidinyl-1-oxyl 3-[3'-Aminopropyl]carbamoyl-2,2,5,5-tetramethylpyrroldinyl-1-oxyl (250 mg) was dissolved in 2 ml methanol with stirring and 0.5 g of potassium bicarbonate and 0.5 ml 2,4-dinitrofluorobenzene added. After 2 hours the mixture was transferred to a separatory funnel, diluted with 15 ml water and extracted with three 15 ml portions of chloroform. The combined organic layers were dried over anhydrous magnesium sulfate, filtered and evaporated. The brown residue was chromatographed on silica gel with ethyl acetate. Evaporation of the solvent yielded an oil which crystallized on addition of ethyl acetate/carbon tetrachloride, yellow crystals (280 mg) m.p. 150°–151°. Anal. Calcd. for $C_{18}H_{26}N_5O_6$: C, 52.92; H, 6.42; N, 17.15. Found: C, 52.60; H, 6.40; N, 16.95. M.W. 408.4

EXAMPLE 1.3

4-(2',4'-Dinitroanilino)-2,2,6,6-tetramethylpiperidino-1-oxyl

4-Amino-2,2,6,6-tetramethylpiperidino-1-oxyl (50 mg) was dissolved in 2 ml methanol with stirring and 0.5 mg potassium bicarbonate and 0.5 ml 2,4-dinitrofluorobenzene was added. A precipitate appeared, and after 12 minutes the reaction mixture was diluted with 15 ml of water and extracted with three 15 ml portions of chloroform. The combined organic extracts were dried over anhydrous magnesium sulfate, filtered and evaporated. Chromatography on silica gel with chloroform gave two yellow bands. The slower moving orange-yellow component was collected and the residue obtained from evaporation of the solvent was recrystallized from chloroform to give orange crystals, m.p. 178°–179°, followed by resolidification and remelting at 189°–190°

Anal. Calcd. for $C_{15}H_{21}N_4O_5$: C, 53.40; H, 6.28; N, 16.61. Found: C, 53.29; H, 6.18; N, 16.38. M.W. 337.3.

EXAMPLE 2.1

3-[2'-($O^{3''}$-Morphino)acetamido]-2,2,5,5-tetramethyl pyrrolidinyl-1-oxyl 3-Bromoacetamido-2,2,5,5-tetramethylpyrrolidin-1-oxyl (139 mg) and 153 mg morphine were refluxed under nitrogen in 4 ml ethanol with 22 mg sodium hydroxide for 2 hours. The reaction mixture was diluted with water and 2 ml of 2 M potassium hydroxide was added. After extraction with chloroform and reextraction of the extracts with water, the chloroform solution was dried with magnesium sulfate and evaporated to give a yellow residue (glass) m.p. 75°–81°. Attempts to recrystallize it failed. Chromatography on silica gel with chloroform/methanol 9:1 gave one main fraction which was the nitroxide radical. The radical was isolated by methanol extraction of the silica gel, rechromatographed, and isolated as before. Evaporation of the methanol, redissolution in chloroform, and centrifugation removed silica gel that was soluble in the methanol. On evaporation 113 mg of a yellow glass was obtained. ESR spectrum: $a_N$ = 14.58 Gauss ($CHCl_3$)

EXAMPLE 2.2

4-[2'-(O³″ Morphino)acetamido]-2,2,6,6-tetramethylpiperidino-1-oxyl

Morphine (153 mg) was dissolved in 4 ml abs. ethanol under nitrogen and 146 mg of 4-bromoacetamido-2,2,6,6-tetramethylpiperidino-1-oxyl were added with stirring. After stirring the solution for 2 hours under reflux it was kept overnight at room temperature. The solution was diluted with water and extracted with chloroform (2 × 30 ml). The combined organic layers were reextracted with 50 ml water (3 drops aq. KOH) and then dried over anhydrous magnesium sulfate. After filtration and evaporation of the solvent there remained a brown oil, which showed one main component by thin layer chromatography (TLC). The product could not be crystallized.

EXAMPLE 2.3

3-(O³″ -Morphinomethyl)-2,2,5,5-tetramethylpyrrolinyl-1-oxyl

A. To a stirred solution of 100 mg (0.58 mmole) of 3-hydroxymethyl-2,2,5,5-tetramethylpyrrolinyl-1-oxyl and 11.49 mg (0.62 mmole) of tri-n-butylamine in 15 ml of absolute ether was added 71.3 mg (0.60 mmole) of thionyl chloride. The reaction was stirred at room temperature for 2 hours and then evaporated. The resulting oil was purified by TLC on silica gel plates with chloroform. The yellow liquid obtained was used directly in the next reaction.

B. Sodium hydride was dissolved in absolute ethanol, and titrated with standard hydrochloric acid to a phenolphthalein end point.

Morphine (30.2 mg, 0.10 mmole) was dissolved in ethanol containing 0.10 mmole of sodium hydride and stirred under nitrogen to which was added 18.8 mg (0.1 mmole) of the above compound dissolved in 1 ml of absolute ethanol and the solution was refluxed for 2 hours. The reaction mixture was then decanted and evaporated. The resulting oil was purified by TLC, using silica gel plates with chloroform-methanol, 9:1, as the eluent. The product was a yellow glass, 15 mg.

EXAMPLE 2.4

3-(O³″ -Morphinoacetamido)-2,2,5,5-tetramethylpyrrolidinyl-1-oxyl

A. Morphine (909 mg) was dried for 4 hours at 50°, 0.01 mm Hg. The dried morphine was dissolved in 18 ml of abs. ethanol and 350 mg dry sodium chloroacetate was added, followed by 125 mg sodium hydroxide. After purging with nitrogen, the solution was stirred and refluxed for four hours. The hot solution was treated with 3.8 ml. ethanolic hydrogen chloride (0.85 M) and then filtered while still warm. On cooling overnight, a precipitate (272 mg) formed which was collected and recrystallized from ethanol/water. On addition of ether to the original filtrate an additional precipitate was obtained which was also recrystallized from ethanol/water. Total yield 600 mg (55 %). On heating this product to 75° in vacuo there was a weight loss corresponding to 0.48 molecule of ethanol or 1.15 molecule of water. The dried compound decomposes at 190°–220° (depends on rate of heating).

Anal. Calcd. for $C_{19}H_{21}NO_5$: C, 66.45; H, 6.16; N, 4.08 Found: C, 65.87; H, 6.98; N, 4.09, 4.07. NMR ($C_5D_5N$) 2.44 ppm (—$CH_3$), 5.08 ppm (—$CH_2$—COO).

B. To 1.03 g (3.0 mmole) O³-carboxymethyl) morphine in 15 ml dry DMF at 0° was added 393 μl (3.0 mmole) isobutyl chloroformate and the mixture stirred for 1 hour under $N_2$. To the stirring solution was added a cooled (0°) solution of 470 mg (3.0 mmole) 3-amino-2,2,5,5-tetramethylpyrrolidinyl-1-oxyl in 5 ml dry DMF. The solution was allowed to come to room temperature over the weekend. The reaction mixture was poured into 60 ml of 10% aqueous sodium chloride, made basic with sodium carbonate, extracted with 4 × 60 ml benzene, dried over sodium carbonate and evaporated in vacuo to a glassy oil. The oil was triturated with 2 × 500 ml petroleum ether and recrystallized from 300 ml boiling cyclohexane. The yellow crystals were filtered and washed with 100 ml petroleum ether. 800 mg (55%) TLC:$R_f$ (0.3), $CHCl_3$:MeOH, 9:1. m.p. 60°–75°

EXAMPLE 2.5

3-[2'-(C³″ -morphino)butyramido]-2,2,5,5-tetramethylpyrrolidinyl-1-oxyl

A. Anhydrous morphine (6.30 g, 22.1 mmoles) and 883 mg (22.1 mmoles) sodium hydroxide in 50 ml absolute ethanol was degassed and refluxed under $N_2$ until dissolution occurred. The ethanol was then removed under vacuum and 40 ml of freshly distilled anhydrous hexamethylphosphortriamide (HMPA) added along with 4.4 g (24.5 mmoles) methyl α-bromobutyrate and 1 g sodium iodide. The mixture was degassed and placed under $N_2$ at 65° for 5 hours. The cooled reaction mixture was poured into 400 ml of ice slurry and the aqueous slurry made basic with aqueous sodium carbonate, extracted with 2 × 200 ml ether. Combined ethereal extracts were washed with 100 ml 5% aqueous sodium carbonate, 100 ml water, 50 ml saturated aqueous sodium chloride, dried over sodium carbonate and evaporated in vacuo. The residue was placed under a vacuum of 0.05 mm Hg for 1 hour and taken up in one liter dry ether to which hydrogen chloride was added until precipitation ceased. The precipitate was filtered, washed with 500 ml ether and taken up in 100 ml water. The aqueous solution was made basic with sodium carbonate and the resulting oil taken up in 100 ml ether, dried over sodium carbonate, evaporated in vacuo and placed under vacuum for 2 hours to yield a viscous yellow oil which crystallized on standing. TLC $R_f$ (0.4) $CHCl_3$:MeOH, 9:1, silica gel.

B. The above ester (500 mg) in 10 ml 2N HCl was refluxed for 2 hours, stripped in vacuo and put under a vacuum of 0.05 mm Hg for 1 hour. The residue was taken up in 5 ml water neutralized to pH 6.5 with 2 N sodium hydroxide, washed with 10 ml of benzene, stripped in vacuo and dried at 0.05 mm Hg for 1 hour. Hot absolute ethanol (10 ml) was added to the residue and the suspension was centrifuged. The supernatant was decanted into 50 ml of acetone and the resulting ppt. was filtered and washed with 10 ml acetone to yield 400 mg of white crystals. TLC $R_f$(0.35)n-BuOH:-$H_2O$:HOAc 8:2:2, on silica.

C. The mixed anhydride was prepared by adding 67 μl (0.508 mmole) isobutyl chloroformate to a solution of 188 mg (0.508 mmole) O³-carboxymethylmorphine (prepared above) in 3 ml anhydrous dimethylformamide (DMF) at 0° (ice bath) and allowing the resulting mixture to stir at 0° for 1 hour under nitrogen. To this was added a cooled solution of 80 mg (0.51 mmole) 3-amino-2,2,5,5-tetramethylpyrrolidinyl-1-oxyl in 1 ml DMF and the mixture allowed to stir under $N_2$ over the weekend. The reaction mixture was poured into 20 ml 10% aqueous sodium chloride and 5 ml 5% aqueous sodium carbonate, which was extracted with 3 × 20 ml benzene and the combined extracts dried with sodium carbonate and evaporated in vacuo. The residue was taken up in 10 ml boiling cyclohexane and an oil was obtained upon cooling. The cyclohexane was decanted and the procedure repeated with 10 ml cyclohexane to obtain pale yellow crystals upon cooling.

Crystals were filtered and washed with 10 ml of petroleum ether to yield 60 mg.

$R_f$ (0.3) $CHCl_3/MeOH$, 9/1, Anal. Calcd. for $C_{29}H_{40}N_3O_5$: C, 68.21; H, 7.89; N, 8.23. Found: C, 67.94; H, 7.95; N, 7.94.

EXAMPLE 2.6

3-(2'-($O^3$-morphino)-3'-methylbutyramido)-2,2,5,5-tetramethylpyrrolidinyl-1-oxyl A. A mixture of 9.45 g (30.2 mmoles) morphine and 1.22 g (30.2 mmoles) sodium hydroxide in 50 ml absolute ethanol was degassed and refluxed under $N_2$ until dissolution. The solvent was evaporated in vacuo and the residue dried at 0.05 mm Hg for 1 hour. The residue was dissolved in 50 ml freshly distilled HMPA, 6.6 g (33.3 mmoles) methyl α-bromo-β-methylbutyrate and 1 g sodium iodide added. The mixture was degassed and heated to 65° for 4 days under $N_2$. The cooled mixture was poured into 400 ml of ice slurry and extracted with 3 × 100 ml ether. The ethereal extracts were combined, washed with 100 ml 5% aqueous sodium carbonate, 100 ml water, 50 ml saturated aqueous sodium chloride, dried over sodium carbonate, evaporated in vacuo and stored at 0.05 mm Hg for 1 hour. The residue was dissolved in 400 ml dry ether and hydrogen chloride added until precipitation ceased. After filtration and washing with 1 liter of dry ether, a white powder was obtained, which was dissolved in 100 ml water and made alkaline with sodium carbonate solution. The resulting oil was taken up in 2 × 200 ml ether, dried over magnesium sulfate, evaporated in vacuo and placed in vacuo overnight to give 5.4 g (45%).

TLC:$R_f$ (0.4), 10% MeOH in $CHCl_3$, silica gel, yellow oil crystallized on standing m.p. 98°–107°.

B. The above ester product (450 mg, 1.2 mmoles) was refluxed in 10 ml 2N hydrochloric acid for 3 hours. The reaction mixture was evaporated in vacuo and the vacuum maintained for 1 hour. The residue was taken up in 10 ml water and the pH adjusted to 6 with 2N sodium hydroxide. The resulting suspension was centrifuged until clear and the supernatant decanted and washed with 20 ml of ether, 20 ml of benzene, then evaporated in vacuo and dried with a vacuum for 1 hour. Hot absolute ethanol (2 ml) was added to the residue and the resulting brown suspension centrifuged and the supernatant decanted into 10 ml of acetone. After filtration and washing with 10 ml of a 2:1 mixture of acetone: abs. ethanol, 100 mg (22%) of off-white crystals was obtained.

TLC:$R_f$ 0.35, n-BuOH:$H_2O$:HOAC 8:2:2.

C. To 77 mg (0.2 mmoles) $O^3$-(isopropylcarboxymethyl)morphine in 2 ml dry DMF at 0° was added 26.2 μl (0.2 mmoles) isobutylchloroformate and the mixture stirred under $N_2$ at 0° for 1 hour. To this mixture was added 31.4 mg (0.2 mmole) 3-amino-2,2,5,5-tetramethylpyrrolidinyl-1-oxyl and the mixture stirred overnight under $N_2$. The mixture was added to 20 ml of water and made basic with sodium carbonate solution and extracted with 2 × 20 ml benzene. The combined benzene extracts were evaporated in vacuo and the residue placed in vacuo (0.05 mm Hg) at 80° for 1 hour. The resulting residue was dissolved in 4 ml boiling cyclohexane and cooled to give pale yellow crystals upon washing with 10 ml pet. ether.

TLC:$R_f$(0.3), $CHCl_3$:MeOH, 9:1. ESR verifies presence of radical. Anal. calcd. for $C_{30}H_{42}N_3O_5$: C, 68.67; H, 8.07; N, 8.01. Found: C, 70.37; H, 9.36; N, 5.56.

EXAMPLE 2.7

$O^3$-(Carbomethoxyhexamethylene-)morphine

Dry morphine (5.7 g, 20 mmoles) and 800 mg (20 mmoles) sodium hydroxide in 50 ml absolute ethanol was degassed under aspirator vacuum and refluxed under nitrogen until the sodium hydroxide had dissolved. The solution was then evaporated in vacuo and the residue dissolved in 40 ml of dry freshly distilled HMPA to which was added 4.2 g (20 mmoles) methyl ω-bromoheptanoate and 1.0 g sodium iodide. The resulting mixture was degassed and put under nitrogen with stirring at 65° for 48 hours. Upon cooling to room temperature, the mixture was poured into a slurry of ice and water (400 ml) and extracted with 3 × 100 ml ether. The combined ether extracts were washed with 100 ml 5% aqueous sodium carbonate, 100 ml water and 50 ml saturated aqueous sodium chloride and dried over anhydrous magnesium sulfate. The dried ethereal extract was stripped in vacuo and placed in 0.05 mm Hg vacuum overnight to yield a yellow oil. The oil was dissolved in dry ether (400 ml) and dry hydrogen chloride bubbled in until precipitation ceased. The white suspension was filtered and washed with 500 ml dry ether, dissolved in 25 ml water and basified with 100 ml 5% aqueous sodium carbonate. The liberated amine was taken up in 200 ml ether, dried over magnesium sulfate and stripped in vacuo. After pumping (0.05 mm Hg) overnight, 5.2 g (61%) light yellow oil was obtained. $R_f$ 0.35 (5% - MeOH/$CHCl_3$; silica gel) NMR ($CDCl_3$) 3.7 (s).

By following the procedures of the foregoing examples. the morphine derivatives can be spin labeled, to provide, for example 3-[7'-($O^3$-morphinoxy)heptamido]-2,2,5,5-tetramethylpyrrolidinyl-1-oxyl.

EXAMPLE 2.8

3-[(N-normorphino)acetamindo]-2,2,5,5-tetramethyl-pyrrolidinyl-1-oxyl

A. Morphine (8.66 g) was acetylated with acetic anhydride (32 g) and pyridine (25 g) at room temperature overnight. After removal of the solvents by azeotroping with benzene, the residue was dissolved in dichloromethane, washed with saturated sodium chloride solution, 2.5% sodium chloride solution, 2.5% sodium carbonate solution, 2N-hydrochloric acid, and finally, saturated sodium chloride solution. Evaporation of the dichloromethane after drying over anhydrous sodium sulfate afforded heroin in a solid state (10.59 g) mp 169°–173°.

A mixture of heroin (10.59 g) and cyanogen bromide (4.3 g) in chloroform (43ml) was heated at 50° for 2 hours. The mixture was cooled in an ice water bath and then poured into ether (170 ml) and stirred for 15 minutes to give a white precipitate, which was washed with hot absolute ethanol (50 ml), and dried over phosphorous pentoxide yielding 8.02 g of cyanonorheroin. m.p. 204°–241° (lit. m.p. 235°–237°)

Cyanonorheroin (3.02 g) was heated at 50° for 5 min. in a solution of potassium hydroxide (3.0 g) in 50% aqueous ethanol (60 ml). Addition of water (180 ml) and then glacial acetic acid (8 ml) gave crystals of cyanonormorphine, which were collected on a filter, washed with water, and dried over phosphorous pentoxide in vacuo affording 6.4 g, m.p. 289° dec (lit. m.p. 288°)

B. Cyanonormorphine (15.4 g) was suspended in 6% hydrochloric acid (450 ml) and heated at 70° for 15 hours with continuous stirring. After being cooled, a precipitate was collected on a filter and dried yielding 14.8 g of N-carbamoylnormorphine, m.p. 268°. Recrystallization from water gave 10.7 g, m.p. 282°, (1st crop), 0.5 g, m.p. 281° (2nd crop) and 0.5 g, m.p. 277° (3rd crop). The mother liquor was purified by column chromatography on silica gel (120 g). Elution with a 1:50 mixture of methanol and chloroform yielded an additional 1.2 g, m.p. 277.5° after crystallization from water. The yield was 79.4%.

C. N-Carbamoylnormorphine (1 g) was gently refluxed in 6% hydrochloric acid (30 ml) for 12 hours. The resulting homogeneous solution was treated with charcoal (200 mg) at 30° for 10 min. After removal of the charcoal, powdered anhydrous sodium carbonate was added carefully to the filtrate until the solution ceased foaming. Addition of 5% sodium carbonate solution brought the pH up to 7.5 to give light gray crystals in the filtrate. The crystals were collected, washed with cold water, dried over phosphorous pentoxide in vacuo, and afforded 860 mg, m.p. 277°, (lit. m.p. 262°–263°; m.p. 276°–277°) of normorphine. Yield, 97.7%.

D. A mixture of normorphine (9.4 g, 0.0347 mole) and powdered sodium bromoacetate (7.1 g, 0.0433 mole) in absolute methanol (175 ml) was gently refluxed for 12 hours, and then cooled to room temperature. Crystals were separated and filtered, washed with cooled water and dried to yield 6.0 g, m.p. 246°. Recrystallization afforded an analytically pure N-carboxymethylnormorphine, 5.9 g, m.p. 269°–271°. Yield, 75%.

Anal. Calcd. for $C_{18}H_{21}NO_6 \cdot H_2O$: C, 62.42; H, 6.10; N, 4.03 Found: C, 62,27; H, 6.12; N, 4.05.

E. N-Carboxymethylnormorphine (500 mg) was treated with acetic anhydride (7 ml) and pyridine (7 ml) at room temperature overnight. After removal of the solvents, trituration of the residue with ether gave a crystalline solid (590 mg), m.p. 258°–259°. Recrystallization from a mixture of methanol and ether afforded an analytically pure diacetate (520 mg) m.p. 266°–8°.

Anal. Calcd. for $C_{22}H_{23}NO_7$: C, 63.91; H, 5.61; N, 3.39. Found: C, 63.95; H, 5.53; N, 3.31.

F. To a solution of diacetyl N-carboxymethyl normorphine (411 mg), 0.943 mmole in dry dimethylformamide (8 ml) and acetonitrile (40 ml) was added 3-amino-2,2,5,5-tetramethylpyrrolidinyl-1-oxyl (193 mg, 1.14 mmoles) in acetonitrile (1 ml) and dicyclohexylcarbodiimide (2.28 mg, 1.14 mmoles) in acetonitrile (1 ml). The mixture was allowed to stir at room temperature for 20 hours. After removal of the precipitate, the filtrate was condensed to leave an oil, which was shaken with a mixture of dichloromethane and water to extract the compound. The dichloromethane layer was purified by preparation TLC. The yellow band with $R_f$ 0.52 (silica gel, 5% methanol-95% chloroform) was collected by cutting and extracted with methanol, and after removal of the solvent, the residue was dissolved in 50% aqueous ethanol containing potassium hydroxide (0.1 g), and heated at 50° for 10 minutes. To the cold solution was added 2N-hydrochloric acid to pH 8. Crystals separated out, 60 mg, which were recrystallized from aqueous ethanol, 57 mg (12.9%), m.p. 218°–221° as an analytically pure sample of 3-[2'-(N-normorphino) acetamido]-2,2,5,5-tetramethylpyrrolidinyl-1-oxyl; ESR ($H_2O$) 3 lines in ratio of 1:1:1, $a_N$ = 16.7 G.

Anal. Calcd. for $C_{26}H_{34}N_3O_5$: C, 66.65; H, 7.31; N, 8.97. Found: C, 66.56; H, 7.27; N, 8.70.

G. Diacetate (see paragraph E) (200 mg, 0.463 mmole) was dissolved in dry dimethylformamide (10 ml) and cooled at 0° with stirring. To the solution was added dropwise isobutylchloroformate (127 mg, 0.926 mmole) and then triethylamine (93 mg, 0.926 mmole). After being stirred for 1.5 hours, 3-amino-2,2,5,5-tetramethylpyrrolidinyl-1-oxyl (145 mg, 1.39 mmoles) in dimethylformamide (0.5 ml) was added and stirred at room temperature overnight, and then water (50 ml) added. The mixture was extracted with dichloromethane. The extracts were washed with water and dried. Evaporation of the solvent left an oil, which was treated by preparative TLC in the same manner as above. The oil with $R_f$ 0.52 was obtained and further worked up in the same manner as above to afford yellow crystals (124 mg, m.p. 218°–221°, 57% yield).

EXAMPLE 2.9

Conjugaton of carboxymethyl morphine with poly-L-lysine (PLL)

Poly-L-lysine hydrobromide (50 mg, Miles Lot. LY 115 A) (1.14 × 10⁻⁶Mole) was suspended in 1 ml dry DMF and 0.241 ml of 1N NaOH was added. The slurry dissolved nearly completely (5 mg residue).

In a separate flask 12.4 mg (0.033 m) of carboxymethyl morphine were dissolved in 1 ml dimethyl (DMF) Q(DMF) (less DMF will not dissolve the acid) and cooled to −15°. To this solution was added 3.28 g (0.033 m) of ethyl chloroformate. The solution was stirred at −15° for 20 minutes after which the poly-L-lysine solution was added followed by the addition of 2 ml of DMF used to wash the flask that contained the poly-L-lysine. A precipitate formed. The reaction was stirred overnight at 0°, diluted with water and dialyzed against distilled water (6 changes). Lyophilization gave 19 mg residue.

Determination of the Degree of Conjugation

The ultraviolet spectrum was measured at 280 nm in a 1 cm cell: d=0.25 when the concentration was 0.287 g/l. in water. $\epsilon_{CMM}^{280} = 1070$, $\beta_{PLL}^{280} = 0$. The degree of conjugation can be determined from this data and the formula $$d = \frac{(X\epsilon_{CMM} + \epsilon_{PLL})W}{XMW_{CMM} + MW_{PLL}}$$

where X = number of haptens per molecule, W = weight of protein conjugate per liter and MW is the molecular weight where CMM refers to the hapten and PLL refers to the protein. Since the molecular weight of the protein was 27,000

X = 30 haptens/molecule.

EXAMPLE 2.10

Conjugation of carboxymethyl morphine to Bovine Serum Albumin (BSA)

Carboxymethyl morphine (240 mg) suspended in 8 ml dry DMF was cooled to −15° and treated with 84 µl isobutyl chloroformate. The solid dissolved while stirring for 30 minutes at −15°. BSA (400 mg) dissolved in 56 ml water containing 2.6 g sodium bicarbonate was added to this solution and the mixture was kept at 0° overnight. It was then dialyzed against distilled water with 4 changes of water (dialysis 1:80) and lyophilized to give 350 mg of conjugate.

Hapten concentration on the protein:

$d = 0.59$  $\epsilon_{BSA}^{280} = 41600$  $\epsilon_{CMM}^{280} = 1070$ $MW_{CMM} = 327$  $MW_{BSA} = 64\,600$ X = 46.6 haptens/molecule.

EXAMPLE 2.11

Conjugation of N-carboxymethylnormorphine to Bovine Serum Albumin

A. To a suspended solution of N-carboxymethylnormorphine (250 mg, 0.74 mmole) in dry dimethylformamide (8 ml) was added isobutylchloroformate (124 mg, 0.89 mmole) and triethylamine (92 mg, 0.89 mmole) with stirring at −15°. After the mixture was continuously stirred and cooled below 0° for 1.5 hours, bovine serum albumin (426 mgm 0.37 mmole) in a cooled 0.7% sodium bicarbonate solution (100 ml) was added gradually with stirring. After the mixture was stirred in the cold room for one day, and then centrifuged (22 min, 4°, 15,500 rpm) to remove the white precipitate the clear solution was dialyzed with distilled (1 l. × 9 times) in the cold room for 3 days. Water was evaporated below 0° in vacuo to leave fluffy white residue (450 mg).

The degree of conjugation (n) was 16 normorphines/molecule.

B. The reaction was done in the same manner as A. using instead isobutylchloroformate (299 mg, 1.63 mmoles) and triethylamine (169 mg, 1.63 mmoles), and finally gave a less soluble residue (151 mg, $n = 38$) than A.

Immunoassays

The compounds of this invention were employed in assaying for a wide variety of ligands. 2,4-Dinitrophenylaniline was accurately assayed, demonstrating that simple small molecules can be determined according to the method employing the compounds of this invention. A number of other compounds having biological activity were also assayed.

While it was found that some variation in procedure was desirable with a few of the assays, for the most part, this did not go to operability but to enhance sensitivity. Also, as is well known, it was found that early harvests of antibodies were not always as good as later harvests of antibodies.

In evaluating an assay for commercial use, not only must the sensitivity for the ligand being assayed be determined, but also cross-reactivity. In some instances cross-reactivity is desirable, where a class of compounds is to be screened, e.g., barbiturates. In other instances substantial specificity will be desired, for example, with a hormone. Therefore, when bonding a hapten to an antigenic protein, these factors will be considered in the molecular engineering.

To demonstrate the analysis for ligands by the subject method, the labeled hapten, 3-(2′, 4′-dinitrophenylamino)2,2,5,5-tetramethylpiperidine-1-oxyl,, was added to the dinitrophenyl antibodies in an aqueous solution. (The antibodies were prepared according to Eisen, et al., JACS, 75, 4583 (1953) and the labeled hapten was prepared in accordance with Hsia, et al, Achives of Biochemistry and Biophysics 132, 466 (1969)). The following procedure was employed. The quantities of the two compounds were chosen by adding small portions of the haptens to the antibody solution until the ESR signal intensity began to rise sharply with addition of each portion. At this point, all the binding sites on the antibodies were occupied by the label and the addition was stopped. Increasing amounts of N-epsilondinitrophenyllysine were than added to the solution. With the addition of increasing amounts of N-epsilon-dinitrophenyllysine to the antibodies-labeled hapten complex, an increase in the ESR signal was observed.

The antibody solution had a concentration of about 2 mg/ml which was equal to about $1-2 \times 10^{-5}$ M of binding site. The labeled hapten was dissolved in 20 percent aq. methanol at about $1-2 \times 10^{-5}$ M concentration. Approximately 10 µl of the antibody solution and 10–20 µl of the labeled hapten solution were combined and varying amounts of $10^{-5}$ M solution of N-epsilon-dinitrophenyllysine in water added, the maximum being 14 µl.

By using appropriate standards, the ESR signal intensity may be related to the concentration of the N-epsilon dinitrophenyllysine in solution. Therefore, by taking an unknown solution suspected of having such a hapten, and introducing a standardized amount of the antibody-hapten complex, one can rapidly determine the concentration of the N-epsilon dinitrophenyllysine in solution.

To illustrate the subject method in relation to a more useful hapten a variety of studies were made with morphine. Morphine antibodies were prepared by injection of the conjugated morphine prepared in Example 2.10 in rabbits as described earlier. The harvested serum was used in the following experiments:

Morphine antibodies were combined with the spin labeled morphine prepared by the method of Example 2.1. The quantities of the two components were chosen by a titration similar to that described for bonding labeled hapten to the dinitrophenyl antibodies. To an aqueous solution of the combined labeled morphine and morphine antibody were added increasing amounts of morphine and the change in the ESR signal intensity was observed.

Codeine is also detected by the same procedure because of its close structural similarity to morphine. Other closely related compounds such as nalorphine and morphine-$O^3$-glucuronide can also be detected, whereas the assay is insensitive to distantly related analogs such as methadone and unrelated compounds such as amphetamines.

As mentioned, a preferred application of the invention is to test for the presence of a drug in a biological fluid. To further illustrate, urine of drug addicts was tested in accordance with the following procedure. Morphine-$O^3$-glucuronide represents the main excretion product of morphine and heroin in humans. About 80% of the total morphine ingested appears as morphine glucuronide in the urine. Since the above spin labeled morphine combined with morphine antibodies can be used to detect both this metabolite and morphine, the assay is especially effective.

Detection of Morphine and its Metabolite in Urine

The urines were added to solutions containing spin labeled morphine of Example 2.1 bound to morphine antibody in about pH 7.9 buffered solution and the amount of increase in the ESR signal was recorded. The increase was recorded as a percentage of the maximum increase of signal that could be obtained in the presence of high concentrations of morphine.

The labeled morphine was first dissolved in a few drops of ethanol and thn dissolved in water to provide a solution of $2 \times 10^{-5}$ M concentration. The antibody concentration in water was about $1-2 \times 10^{-5}$ M based on binding sites. Included in the antibody solution was approximately 0.4 M Tris or 0.6 M sodium borate to provide a pH of 7.5 with the former and 7.9 with the latter. The pH will drop due to dilution and the presence of acid in the urine. To 20 μl of urine was added sufficient sodium dichromate to provide a concentration of $2 \times 10^{-2}$ M in order to destroy any interfering reducing substances. The urine sample was then combined with 10 μl of an equivolume mixture of the antibody solution and the labeled morphine solution.

The data given for urine samples 1-5 in Table III are the percent increases for a randomly selected set of urine samples from people who had taken no narcotic agents for at least one week. Urine samples 6 - 10 in Table III were from known heroin addicts and patients known to be taking codeine. The high percentage increases for the latter group demonstrate the efficacy of the assay technique.

TABLE III

| Controls Urine Sample No. | % Signal Increase | Study Group Urine Sample No. | % Signal Increase | Drug Taken |
|---|---|---|---|---|
| 1) | 6 | 6) | 58 | heroin |
| 2) | 3 | 7) | 81 | heroin |
| 3) | 5 | 8) | 100 | heroin |
| 4) | 7 | 9) | 75 | codeine |
| 5) | 4 | 10) | 62 | codeine |

As a demonstration of the sensitivity of the method, the results of the ligand assay technique were compared with the present commercial TLC test. In the TLC test, morphine is removed from urine by solvent extraction and, after evaporation of the extracts, the residue is analyzed by thin layer chromatography. Since the morphine glucuronide is not extracted with benzene, only morphine is detected, and the test is relatively insensitive. In Table IV the results of the two assay methods are compared for the urine from a single heroin user who admitted taking the drug on the second and fifth days. It is apparent from the data that the ligand assay technique permits detection of the drug even three days after it was taken. This conclusion was verified by comparing the data with data obtained on the same urine samples using an improved TLC technique in which the morphine glucuronide is first hydrolyzed with acid to give free morphine. These data are included for comparison in Table IV. Although the improved TLC technique is still not as sensitive as the hapten assay technique, the results provide confirmation that the labeled ligand technique gives valid data.

TABLE IV

| Day | % Signal Increase | TLC Results | Improved TLC Results |
|---|---|---|---|
| 1 | 17 | − | + |
| 2 | 57 | + | + |
| 3 | 32 | − | + |
| 4 | 26 | − | + |
| 5 | 47 | + | + |
| 6 | 26 | − | + |
| 7 | 16 | − | − |
| 8 | 8 | − | − |
| 9 | 40 | + | + |

By employing compounds of the subject invention in combination with antibodies prepared in accordance with the subject invention, a rapid and convenient method is provided for accurately determining a wide variety of biologically interesting materials. Furthermore, by contrast with prior art methods, the subject method provides a higher degree of accuracy and freedom from other interfering materials. Since the radical ligand analog can be prepared with minimum interference with spatial geometry and salient polar features of the molecule, and there is no concern with retention of the physiological activity of the molecule to be assayed, the method is extremely versatile. In addition, reagents can be prepared and kept for long periods of time without significant change in activity or easily calibrated, and determination rapidly made without extensive manipulation or long periods of waiting. Isolation or substantial separation of the material to be assayed from other groups is generally not required. The use of radioisotopes which are frequently dangerous and have difficulties in manipulation is avoided. Also, the subject method does not suffer from the disadvantages of the colormetric techniques, which cannot be carried out in opaque or turbid solutions.

Although the foregoing invention has been described in some detail by way of illustration and example for purposes of clarity of understanding, it will be obvious that certain changes and modifications may be practiced within the scope of the appended claims.

What is claimed is:

1. A spin labeled reagent having the morphine structure and of the formula:

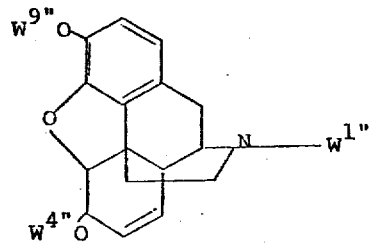

wherein:
one of $W^{1''}$ and $W^{9''}$ is $-X^*-A^*$;
when other than $-X^*-A^*$
$W^{1''}$ is methyl; and
$W^{9''}$ is hydrogen, methyl or glucuronyl;
$W^{4''}$ is hydrogen or acetyl;
$-X^*$ is

wherein Z is aliphatic hydrocarbylene of from 1 to 7 carbon atoms, having from 0 to 1 site of ethylenic unsaturation and bonded to said morphine structure; and —A* is of the formula:

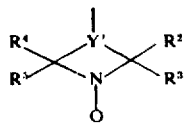

wherein $R^2$-5 is alkyl of from 1 to 3 carbon atoms and Y' is a trivalent aliphatic hydrocarbylene of from 1 to 3 carbon atoms, having from 0 to 1 site of ethylenic unsaturation.

2. A spin labeled reagent according to claim 1, which is 3-{2'-($O^{3''}$ -morphino)acetamido}2,2,5,5-tetramethylpyrrolidinyl-1-oxyl 3. A spin labeled reagent according to claim 1, which is 4-{2'-($O^{3''}$ morphino)acetamido}2,2,6,6-tetramethylpiperidino-1-oxyl.

4. A spin labeled reagent which is 3-($O^{3''}$ -morphinomethyl-2,2,5,5-tetramethylpyrrolinyl-1-oxyl.

5. A spin labeled reagent according to claim 1, which is 3-{2'-($O^{3''}$ -morphino)butyramido}-2,2,5,5-tetramethylpyrrolidinyl-1-oxyl.

6. A spin labeled reagent according to claim 1, which is 3-{(N-normorphino)acetamido}-2,2,5,5-tetramethylpyrrolidinyl-1-oxyl.

* * * * *